US009895456B2

(12) United States Patent
Verschuur

(10) Patent No.: US 9,895,456 B2
(45) Date of Patent: Feb. 20, 2018

(54) STERILISATION CONTAINER

(71) Applicant: KILLARA I.P. PTY LTD, Lilydale, Victoria (AU)

(72) Inventor: Mark Verschuur, Victoria (AU)

(73) Assignee: KILLARA I.P. PTY LTD, Lilydale, Victoria (AU)

( * ) Notice: Subject to any disclaimer, the term of this patent is extended or adjusted under 35 U.S.C. 154(b) by 0 days.

(21) Appl. No.: 14/783,884

(22) PCT Filed: Apr. 15, 2014

(86) PCT No.: PCT/AU2014/050014
§ 371 (c)(1),
(2) Date: Oct. 12, 2015

(87) PCT Pub. No.: WO2014/169352
PCT Pub. Date: Oct. 23, 2014

(65) Prior Publication Data
US 2016/0051329 A1    Feb. 25, 2016

(30) Foreign Application Priority Data
Apr. 15, 2013    (AU) .................. 2013901524

(51) Int. Cl.
*A61L 2/07* (2006.01)
*A61B 50/30* (2016.01)
(Continued)

(52) U.S. Cl.
CPC ................ *A61L 2/07* (2013.01); *A61B 50/30* (2016.02); *A61L 2/20* (2013.01); *A61B 90/70* (2016.02);
(Continued)

(58) Field of Classification Search
CPC .......... A61L 2/07; A61B 19/026; A61B 19/34
See application file for complete search history.

(56) References Cited

U.S. PATENT DOCUMENTS 6,000,534 A * 12/1999 Koomruian, Jr. .... A45C 11/005
134/901
6,793,882 B1  9/2004 Verschuur
(Continued)

FOREIGN PATENT DOCUMENTS

WO    1998/006443 A2    2/1998

OTHER PUBLICATIONS

International Search Report for Application No. PCT/AU2014/050014 dated May 28, 2014.
(Continued)

*Primary Examiner* — Sean E Conley
(74) *Attorney, Agent, or Firm* — The Dobrusin Law Firm, P.C.

(57) ABSTRACT

A container for sterilizing a medical object and storing a sterilized medical object, the container including: a container body including a first opening in a first end of the container for passage of the medical object into the internal cavity, the internal cavity including a removably insertable platform having a receiving surface to receive and support the medical object, the platform keyed to be retained in a fixed position between the first end of the container body and a second end of the container body; a first seal for closing the first opening; and a vapor permeable sterility barrier for maintaining sterility of the internal cavity and allowing the passage of vapor.

19 Claims, 5 Drawing Sheets

(51) Int. Cl.
   *A61L 2/20* (2006.01)
   *A61B 50/00* (2016.01)
   *A61B 90/70* (2016.01)

(52) U.S. Cl.
   CPC ............ *A61B 2050/0054* (2016.02); *A61B 2050/0064* (2016.02); *A61B 2050/0066* (2016.02); *A61L 2202/122* (2013.01); *A61L 2202/15* (2013.01); *A61L 2202/18* (2013.01); *A61L 2202/181* (2013.01); *A61L 2202/24* (2013.01)

(56) References Cited

U.S. PATENT DOCUMENTS

| | | | |
|---|---|---|---|
| 2005/0103649 A1* | 5/2005 | Vulcu | A61F 9/0061 206/5.1 |
| 2005/0238530 A1 | 10/2005 | Frieze et al. | |
| 2007/0034538 A1 | 2/2007 | Landis | |
| 2013/0000262 A1 | 1/2013 | Richart | |

OTHER PUBLICATIONS

DuPont Technical Reference Guide for Medical and Pharmaceutical Packaging published in Oct. 2011 (noted on p. 2).
Safety Data Sheet for Acryrex® PMMA, Version 1, Print Date Nov. 30, 2015.
European Search Report, Application No. EP 14784626.5 dated May 30, 2017.

\* cited by examiner

STERILISATION CONTAINER

FIELD OF THE INVENTION

The present invention relates to a container for sterilising a medical object and storing a sterilised medical object.

BACKGROUND OF THE INVENTION

Surgical operations must be carried out under strict conditions of sterility to minimise infection risk in the patient. To this end, a sterile field is set up in the operating theatre around the patient. Any theatre staff, such as surgeons or nurses, who come into physical contact with the patient during surgery must rigorously scrub and wear sterile surgical gloves. All objects and equipment used in surgery must also be sterile.

Surgical equipment is frequently supplied inside sterile packaging which ensures that the equipment inside the packaging is sterile and remains so whilst the packaging is unopened. However, storage, handling, and distribution of the packaging cause the outer surface of the packaging to become non-sterile. To account for this whilst maintaining the sterile field in the operating theatre, surgical teams include a non sterile nurse who opens the packaging containing the sterile surgical equipment and exposes the sterile equipment to a nurse within the sterile field. The nurse within the sterile field then removes the sterile equipment from the packaging. Provided that the non-sterile nurse does not touch the equipment, sterility of the sterile field is not compromised.

A number of pieces of medical and surgical equipment are reusable. In order to reuse such equipment, it is necessary to sterilise the equipment before use in the next operation. Sterilisation of medical and surgical equipment is commonly carried out in an autoclave in which steam at elevated pressure at a temperature of around 134° C. sterilises the equipment.

Although autoclaving is an effective sterilisation method, difficulties can arise where the medical and surgical equipment is delicate. During the autoclave operation, a number of pieces of equipment may be loaded into the autoclave at any one time. This can lead to breakage of delicate equipment. Moreover, it can be difficult to maintain the sterility of the equipment when it is removed from the autoclave and stored for use in the next operation.

An improved means for sterilising medical devices is sought that addresses at least some of the aforementioned problems.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

The present invention is directed towards providing an apparatus for sterilising a medical object and storing a sterilised medical object. The medical object may be a medical instrument, such as an endoscope or endoscopic telescope.

In one aspect of the invention there is provided a container for sterilising a medical object and storing a sterilised medical object, the container including: a container body including a first opening in a first end of the container for passage of the medical object into the internal cavity, the internal cavity including a removably insertable platform having a receiving surface to receive and support the medical object, the platform keyed to be retained in a fixed position between the first end of the container body and a second end of the container body; a first seal for closing the first opening; and a vapour permeable sterility barrier for maintaining sterility of the internal cavity and allowing the passage of vapour.

The sterility barrier preferably allows passage of vapour from the internal cavity to an outside environment and vice versa.

Preferably, the container is adapted for a steam sterilisation process, such as in an autoclave.

A range of different methods can be used so that the platform is keyed to be retained in the container body. Each of the container body and the platform may be shaped to engage with each other so that the platform is retained in a fixed position within the container. In one embodiment, edges of the platform engage with reciprocal channels of the container body to fix the container body in place. In another embodiment the platform is keyed to be retained in the container body via a snap fit mechanism with the container body, which when the snap fit mechanism is engaged the platform is fixed in position within the container body.

The platform may include a first end and a second end. When positioned within the container the first end and the second end of the platform are in proximity to or adjacent the first end and the second end of the container respectively. When the container is positioned on a substantially horizontal surface, such as during storage or during sterilisation, the platform is oriented so that the second end of the platform is below the first end. This orientation assists with the drainage of moisture from the object on the platform and from the platform itself. It may also assist drainage of moisture from the container through the second end.

In an embodiment, the first end of the container and the second end of the container define a longitudinal axis of the container, wherein the platform has a length that is aligned with the longitudinal axis of the container, and the receiving surface of the platform is in a plane that faces orthogonal to the longitudinal axis of the container. Preferably, the length of the platform extends across at least 50% of the distance between the first end and the second end of the container. More preferably, the length of the platform extends at least 60%. Even more preferably, at least 70%. Even more preferably, at least 80%. Most preferably, the length of the platform extends substantially across the distance between the first end and the second end, with a first head space between a first end of the platform and the first end, and a second head space between a second end of the platform and the second end.

In an embodiment, the vapour permeable sterility barrier is a non-wettable vapour permeable sterility barrier. The non-wettable vapour permeable sterility barrier preferably allows the passage of vapour, which is preferably steam, into the internal cavity. Preferably the non-wettable vapour permeable sterility barrier is hydrophobic. A hydrophobic vapour sterility barrier may allow the passage of water and water vapour therethrough, but due to the hydrophobic nature prevents surfaces of the barrier from being wetted by water. As the barrier cannot be wetted, strikethrough cannot occur. Strikethrough is a problem that occurs when a porous membrane (such as a permeable sterility barrier) becomes wetted. Wetting of the permeable sterility barrier may allow the transfer of pathogens to pass through the barrier, compromising sterility.

In an embodiment, the vapour permeable sterility barrier forms part of the first seal. However, the vapour permeable sterility barrier may instead be a part of the container body. Preferably, the vapour permeable sterility barrier is insert moulded to the first seal.

In an embodiment, the first seal includes: a threaded portion for threaded engagement with a reciprocal threaded portion on the first opening of the container body to seal the container, an outer shell portion, and the vapour permeable sterility barrier.

It is preferred that the vapour permeable sterility barrier is fixedly connected to the first seal.

It is preferred that the vapour permeable sterility barrier forms at least a portion of an external surface of the first seal.

It is preferred that the first seal includes a guard that extends across at least a part of an external surface of the vapour permeable sterility barrier to protect the vapour permeable sterility barrier from damage. The guard may be a mesh structure that extends across the surface of the sterility barrier, or alternatively may be a contiguous structure that physically covers a portion of the surface of the sterility barrier. Preferable the guard covers less than 70% of the surface of the sterility barrier, more preferably less than 60%, even more preferably less than 50%.

It is preferred that the guard is formed from plastic. More preferably, the guard is integrally formed with the outer shell portion of the first seal.

In an embodiment, the platform is additionally keyed to retain the medical object on the surface of the platform. The platform is preferably keyed to the shape of the medical object helps to prevents movement of the medical device within the container. This helps to prevent damage to the medical device during movement of the container. Preferably the platform includes drainage holes to prevent a liquid from pooling around the medical object. This assists in maintaining the medical device in a dry state during storage. Additionally, as the medical device is retained in place by the platform, wetting of the device from any moisture retained within the container is minimised.

In an embodiment, the container body is formed from a polymer blend including at least one polymer and a hydrophobic additive or a thermoplastic elastomeric material.

Preferably the hydrophobic additive is a fluoro chemical. Preferably the fluoro chemical is present in the polymer blend at 2 to 5 weight percent. More preferably the fluoro chemical includes a polypropylene carrier. Preferably the thermoplastic elastomeric material is added in an amount of greater than zero up to 25 wt %. The advantage of the hydrophobic polymer material addition is that the material can be blow moulded into the container body. This provides for significantly easier construction than applying a separate hydrophobic layer to the internal surface of the container body. The thermoplastic elastomeric material addition makes the container wall in the region of the bellows more pliable and reduces the compressive force needed to compress or concertina the container.

In some circumstances, it may be desirable to apply a separate hydrophobic layer, such as a hydrophobic coating, to the internal surface of the container body.

Regarding the above described aspects, by placing the medical device in the container and sealing the opening in the container, the medical device is confined within the container and therefore protected from damage by contact with other objects during sterilisation. Sealing the medical device within the container also prevents the entry of bacteria into the container after sterilisation is complete. Thus the container provides a convenient means of storage that can maintain the sterility of the medical device.

In an embodiment, the container further includes a second opening in the second end, and a second seal for closing the second opening. Preferably the vapour permeable sterility barrier forms part of the second seal. In such cases, it is preferred that the vapour permeable sterility barrier is insert moulded to the second seal. Also, it is preferred that the second seal includes a guard that extends across at least a part of an external surface of the vapour permeable sterility barrier to protect the vapour permeable sterility barrier from damage.

More preferably, both of the first seal and the second seal include a vapour permeable sterility barrier. Alternatively, the second end is formed as a closed end that is not removable from the container body.

In an embodiment the vapour permeable sterility barrier includes a microporous membrane. Preferably the microporous membrane is formed from a polymeric material. It will be appreciated that the microporous membrane should be resistant to failure under the sterilisation conditions. For example, if the container is designated for use in an autoclave, the microporous membrane needs to be capable of withstanding elevated temperatures and pressures. A suitable microporous membrane material may be KIMGUARD sterilisation wrap provided by Kimberly-Clark healthcare, or the ASPIRE sterilisation membrane provided by GE. Other materials may also be used. It is preferred that the vapour permeable sterility barrier is formed from a material selected from the group consisting of polypropylene, polyesters and polytetrafluoroethylene.

In an embodiment the container body further includes a neck portion that is narrower than the container body, the neck portion having an internal surface that engages with the medical object to prevent the medical object from moving within the container. Preferably the neck portion includes a support rib. The neck provides support and strength to the head whilst also creating an ergonomic grip feature.

In an embodiment the container includes a collapsible or deformable bellows portion. Advantageously, the inclusion of a collapsible or deformable bellows portion allows the object inside the container to be easily accessed during a surgical operation. When in use in a surgical operation, a non-sterile nurse may remove the seal and collapses or deforms the bellows portion of the container. Consequently, the sterile object inside the container is at least partially exposed so that the sterile nurse can access the exposed part and remove the sterile object from the container. The container allows the sterilised object to be removed without the non-sterile nurse having to touch the sterile inner part of the container or the sterile equipment inside the container. Similarly, the sterile nurse does not have to touch the non-sterile outer surface of the container.

In an embodiment the container body includes an elongated portion so that the container is suitable for receiving an elongate object. Preferably the elongate portion is between the bellows portion and the second end. Preferably the elongate portion is offset in at least one plane from a parallel axis that extends from a centre of the first end to the second end.

In an embodiment the container is used to sterilise medical objects in an autoclave or similar. Preferably the container is formed from materials that are heat stable at temperatures of up to about 140° C. and materials that are pressure stable at pressures of up to 100 kPa gauge.

In an embodiment the container is relatively enlarged at the first end. This allows easier insertion of an object into the container. It also enables the container to hold objects having a relatively enlarged part, such as an endoscopic telescope.

In another aspect of the invention there is provided a method for sterilising an object, the method including: placing the object into a container as previously described, sealing the container, and placing the container in a sterilising environment for sufficient time to sterilise the object. Preferably the sterilising environment is within an autoclave. Although autoclaving is the preferred sterilising method, other sterilising methods may be used. Such methods may include placing the container in a sterilising fluid. In such cases, the vapour permeable sterility barrier should also be permeable to the sterilising fluid.

Preferably the step of sealing the container includes affixing a vapour permeable sterility barrier to a rim of the opening. The seal may be affixed to the rim of the opening by an adhesive. Alternatively, the seal may be a cap that is screwed onto a threaded portion of the rim, the cap including the vapour permeable sterility barrier. The vapour permeable sterility barrier may be permeable to other fluids. However, it is preferred that the vapour permeable sterility barrier is not permeable to bacteria, or at least impedes the passage of bacteria therethrough.

It is preferred that the seal is a tamper-evident seal that can only be removed from the container in a tamper-evident manner, for example by rupturing the seal. Such tamper-evident lids are well known and will not be described further.

In another aspect of the invention there is provided a method of removing a sterilised object from a container as previously described having a collapsible or deformable bellows portion, the method including: removing the first seal, collapsing or deforming the bellows portion so that the object extends at least partially out of the container, and removing the object from the container. Preferably the step of collapsing or deforming the bellows portion causes the first end to move relatively closer to a second end. The step of removing the first seal may occur as a result of the object rupturing the first seal on collapse or deformation of the bellows.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

The container for sterilising a medical instrument and storing a sterilised medical instrument will now be described with reference to the Figures.

Figure 1:
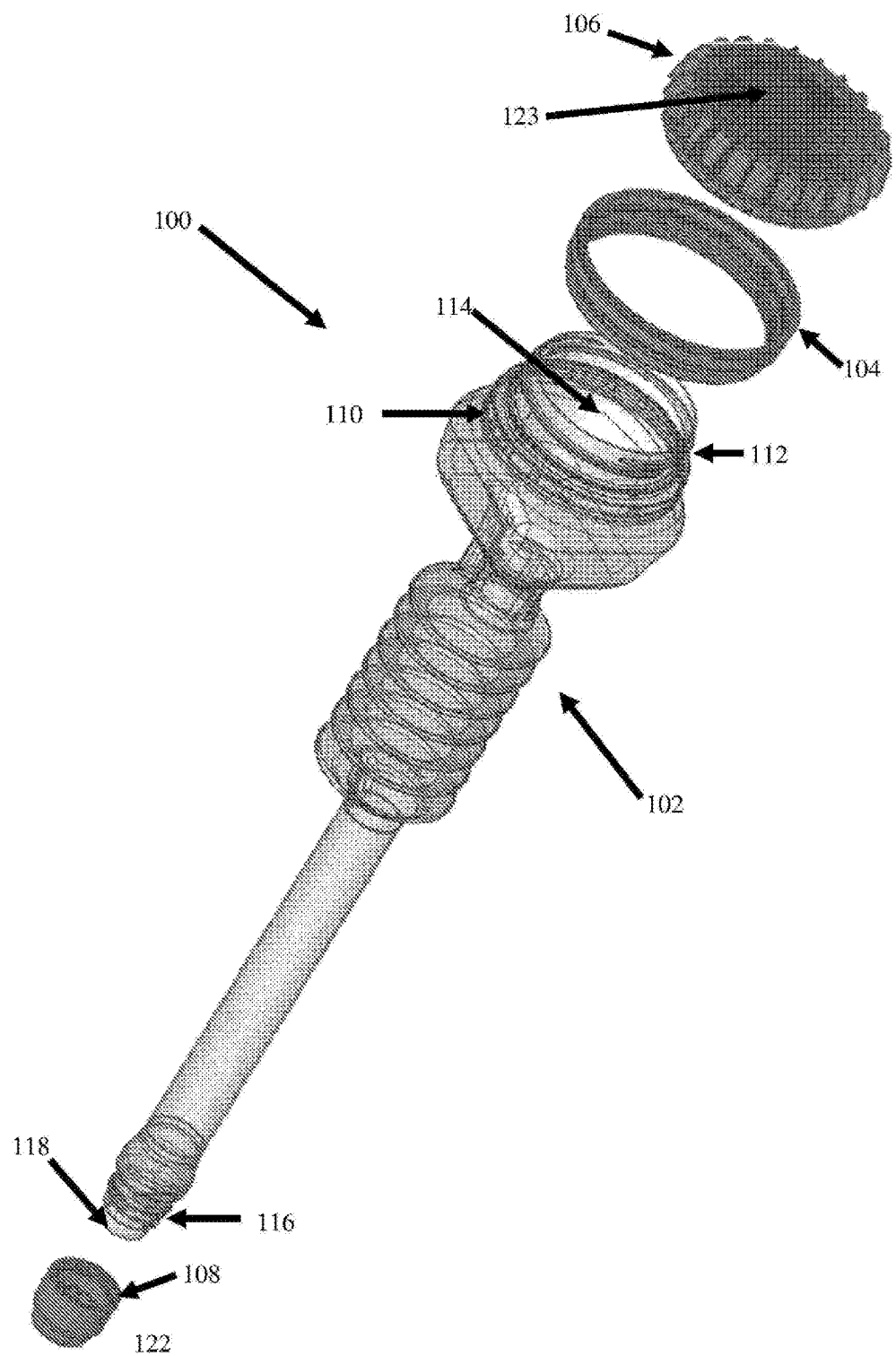
FIG. 1 shows a perspective view of an embodiment of a container for storing a medical object such as an endoscope.

FIG. 1 shows an embodiment of a container for storing a medical instrument according to the present invention. The container 100 includes a container body 102, a tamper evident ring 104, a first cap or seal 106, and a second cap or seal 108.

The container body includes a mount 110 for receiving the tamper evident ring 104 and a first threaded portion 112 for threaded engagement with the first cap 106 to seal a first opening 114, and a second threaded portion 116 for threaded engagement with the second cap 108 to seal a second opening 118. Although the tamper evident ring 104 is shown as a separate component from the first cap 106, they are actually fixedly connected prior to engagement with the container body 102. On disengagement from the container body, the temper evident ring 104 and the first cap 106 become separated. This separation provides evidence that the container has been opened or tampered with.

The first opening 114 is for insertion an object, such as an endoscopic telescope, into the internal cavity of the container body 102. The container body 102 may be shaped to receive a specific type of object. In this embodiment the container body 102 has an elongate shape that is configure to receive an endoscopic telescope (not shown). After the object is placed inside the container body 102, the first cap 106, including the tamper evident seal 104, is screwed onto the threaded portion 112 to close the first opening 114. The second opening 118 is similarly closed by screwing the second cap 108 onto the second threaded portion 116 of the container body 102. Once both openings are closed, the object is held within the container 100 and sealed from the external environment. The container 100 including the object can then be placed in a sterilisation environment for a sterilisation operation.

The first cap 106 includes a vapour permeable sterility barrier 120. In this case, the vapour permeable sterility barrier 120 is insert moulded within the first cap 106. This vapour permeable sterility barrier 120 allows the ingress and egress of sterilisation fluids. Sterilisation fluids are able to enter into the container 100 to sterilise the object retained within, and then exit. In this embodiment, the second cap 108 also includes a vapour permeable sterility barrier 122. It will be appreciated that while a vapour permeable sterility barrier is required, it does not necessarily need to form a part of the first cap 106 or the second cap 108.

In this case, the first cap 106 includes a shield 123 which overlies at least a portion of the external surface of the vapour permeable sterility barrier 120. This shield 123 protects the vapour permeable sterility barrier from damage, such as physical impacts.

The container body 102 is manufactured from a polymer blend that includes a hydrophobic additive. This causes the surfaces of the container body 102 to have hydrophobic properties. This assists in the removal of water vapour from within the container 100 which assists in maintaining the internal environment of the container 100 in a sterile state after sterilisation. In some instances liquids that are retained within the container 100 after sterilisation can interact negatively with the vapour permeable sterility barriers 120 and 122. In some instances, if the vapour permeable sterility barriers 120 and 122 become wetted, a problem known as strikethrough can occur. Strikethrough can result in the sterility of the internal environment within the container 100 being compromised. Bacteria and/or other pathogens may be able to ingress through any wetted portions of the vapour permeable sterility barriers 120 and 122. To further mitigate the potential for strikethrough, a vapour permeable sterility barrier that is selective only to gaseous phases (including water vapour) may be employed. If liquids such as water are unable to pass through the vapour permeable sterility barriers 120 and 122, then the likelihood of strikethrough occurring will be minimised. Additionally, the vapour permeable sterility barriers 120 and 122 may be formed from a hydrophobic material. This stops the vapour permeable sterility barriers from being wetted, thus preventing strikethrough from occurring.

Figure 2:
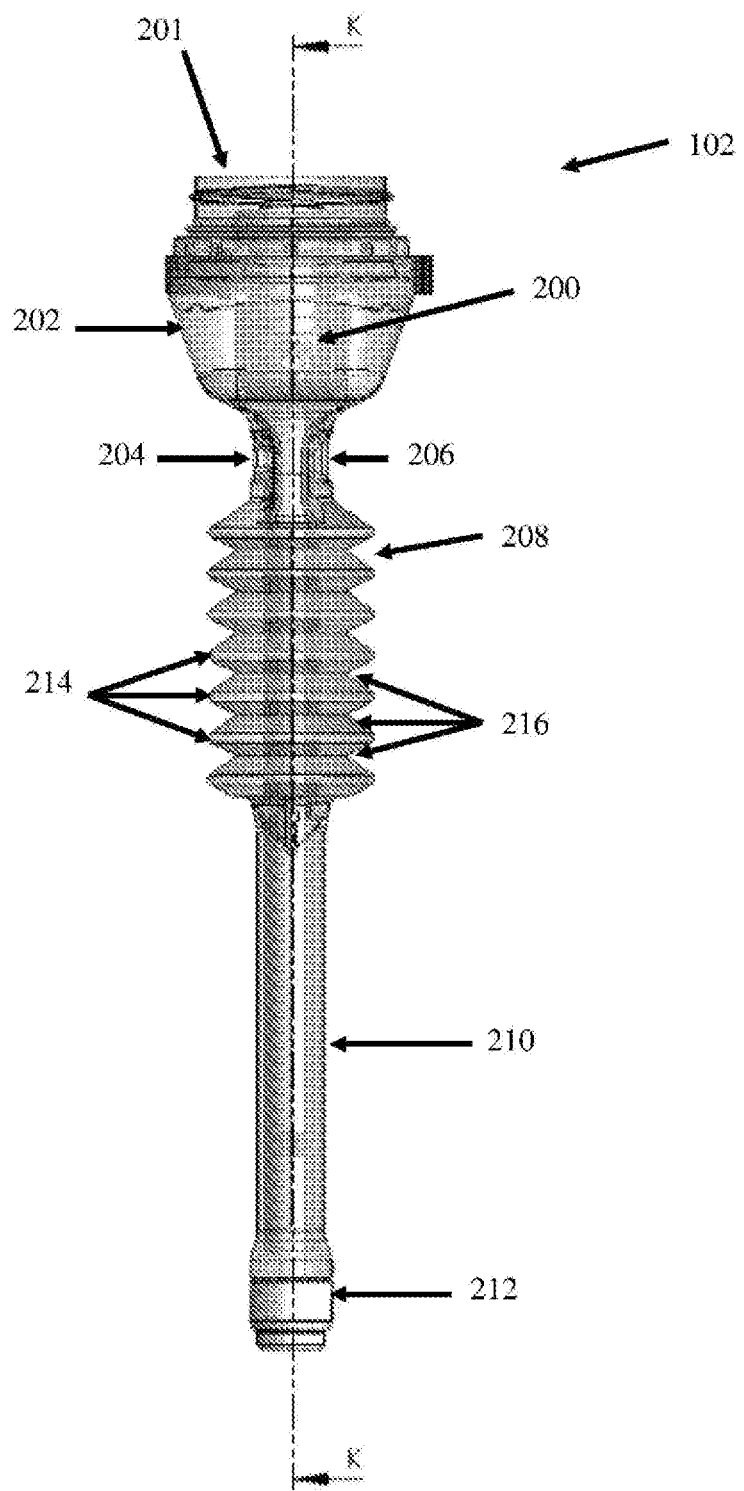
FIG. 2 shows a top down view of the embodiment shown in FIG. 1.

FIG. 2 shows a top down view of the container body 102 shown in FIG. 1. The container 102 has a medical instrument 200 retained therein. As can be seen, the container body 102 is shaped to accommodate the instrument 200. The container body 102 includes a first end 201 having a wide upper portion 202 that is shaped to retain a wide head of the instrument, a narrow neck portion 204 with a support rib 206, a bellows portion 208, an elongate portion 210, and a second end 212.

The bellows portion 208 of the container body 102 is collapsible or deformable. The bellows portion 208 includes a number of corrugations or flutes 214 formed in the outer wall of the container body 102. This allows the bellows portion 208 to be collapsed or deformed in a concertina fashion. To this end, the collapsible or deformable portion includes a plurality of fold lines 216 extending around the container body 102 about which the corrugations or flutes 214 are collapsed together. The effect of collapsing the bellows portion 208 in this manner is to bring the first end 201 and the second end 212 closer together.

Figure 3:
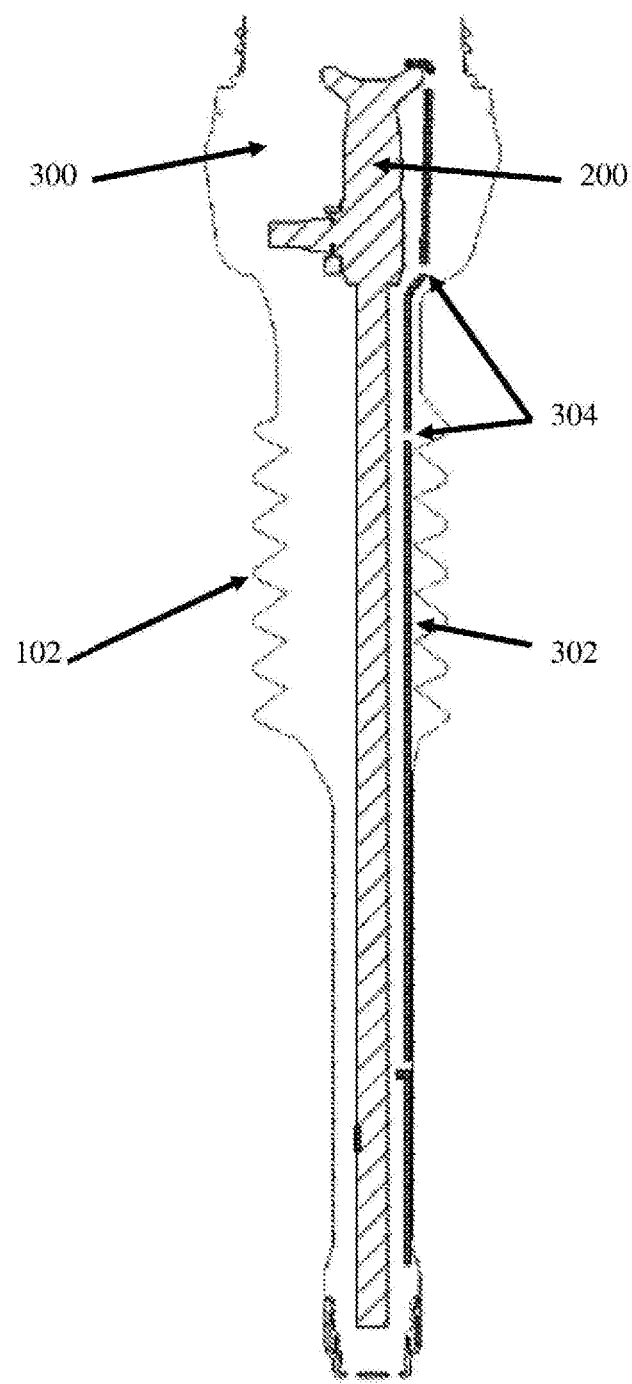
FIG. 3 is a sectional view through K-K of the embodiment shown in FIG. 2.

FIG. 3 shows a sectional view through section lines K-K in FIG. 2. The container body 102 having an internal environment 300 that includes a platform 302. The platform 302 is in a keyed relationship with the container body 102. This keyed relationship locks the platform 302 in position within the container body 102, preventing relative movement between the platform 302 and the container body 102. In this case, the platform 302 extends substantially the full length of the container body 102 with head space between ends of the platform 302 and each of the first and second ends of the container body 102. In this way, the platform 302 is able to support the medical instrument 200 substantially along the length of the container body.

The platform 302 is removable and reinsertable into the container body 102. This allows platform 302 to be removed from the container 100 so that a medical instrument 200 may be placed on the platform 302 and then reinserted into the container 100 along with the medical instrument 200. The platform 302 snap fits into position within the container body 102 to retain the platform 302 in fixed position relative to the container body 102. When it is desired to remove the platform 302 from the container 100, the snap fit connection can be disengaged allowing the platform 302 to be disconnected from the container body 102 and removed from the container 100.

An object, such as a medical instrument 200 is held within the internal environment 300 of the container body 102 on top of the platform 302. The platform 302 may include a number of drainage holes 304 to prevent any liquids (such as those introduced to sterilise the object 200) from pooling around the object 200.

In this case, the platform 302 is keyed to the shape of the object 200 to be sterilised. This allows the object 200 to be retained in position on the platform 302 within the container 100. This prevents movement of the object 200 within the container 100, for example when the container 100 is moved or rotated during transfer or storage.

One or more retention devices associated with the platform 302 may be used. The retention devices may be fixing devices such as ties or detachable such as hook and loop fastening straps which hold the object in position.

Figure 4:
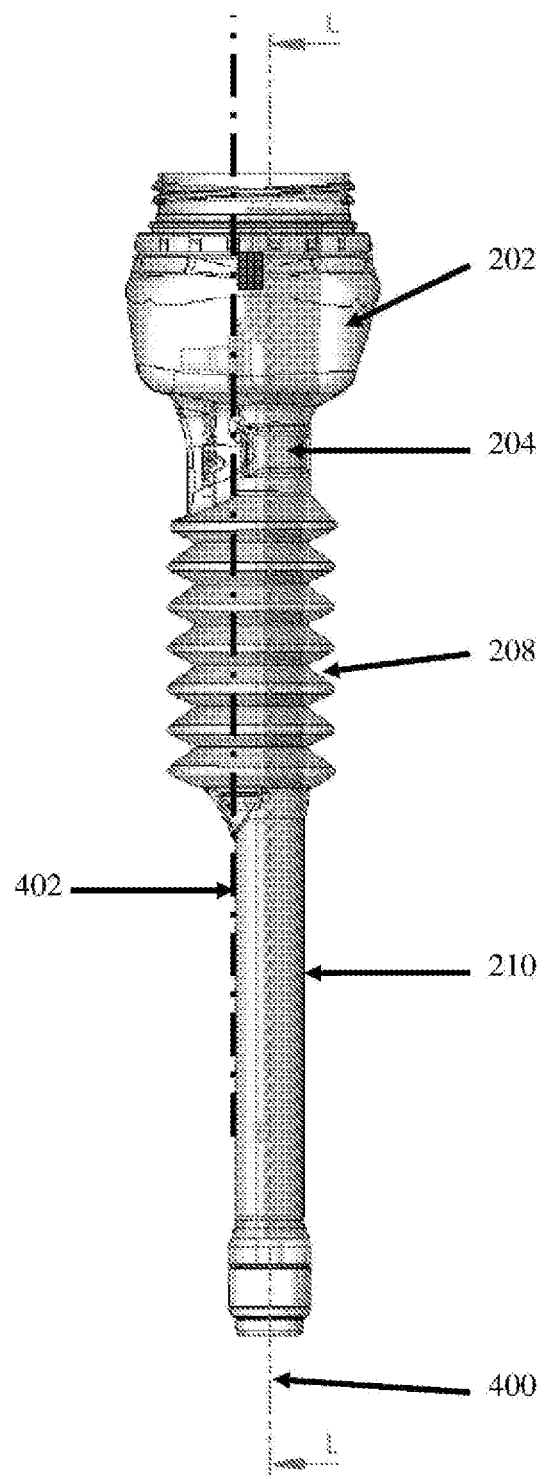
FIG. 4 is a side view of the embodiment shown in FIG. 1.

FIG. 4 shows a side view of the embodiment shown in FIG. 1. As can be seen the axis 400 that runs through the centre of the elongate portion 210 and neck portion 204 is axially offset from the central axis 402 of the container body 102 that runs through the centre of the upper portion 202 and the bellows portion 208. This arrangement helps to prevent the container body 102 from rolling.

Figure 5:
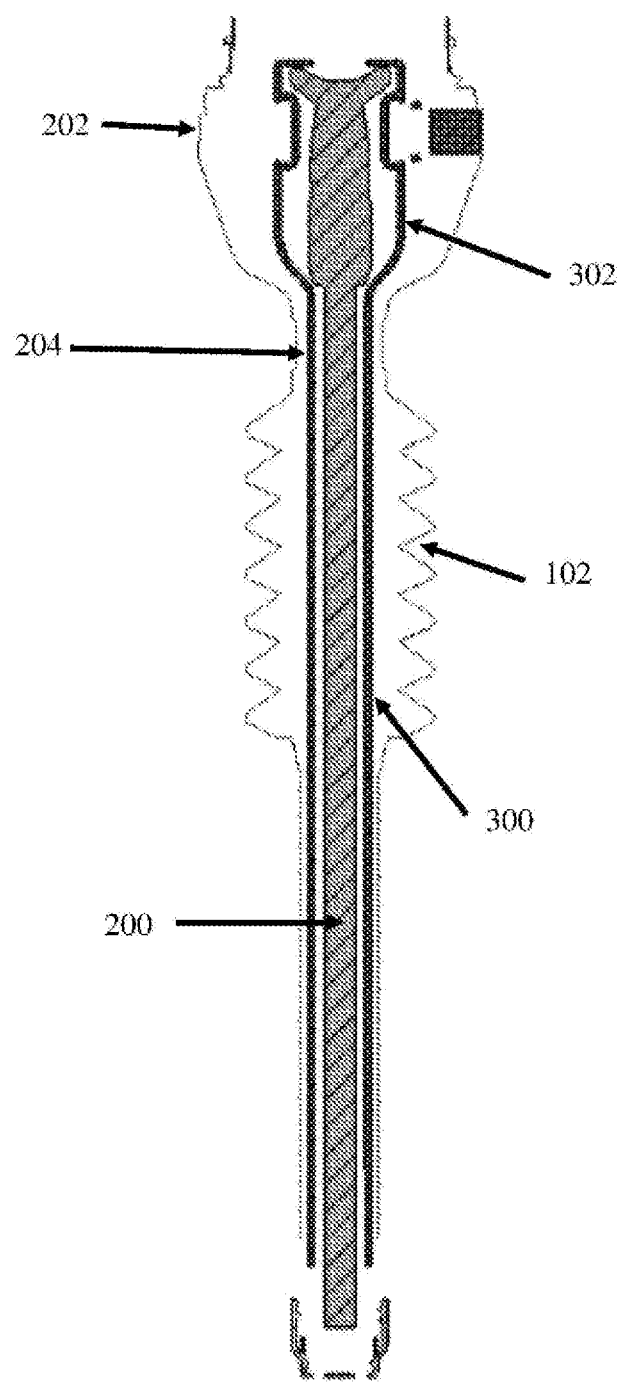
FIG. 5 is a sectional view through L-L of the side view shown in FIG. 3.

FIG. 5 shows a sectional view through section lines L-L of axis 400. As previously, the container body 102 has an internal environment 300 that includes a platform 302 upon which an object 200 to be sterilised can be placed. The container body 102 includes a neck portion 204. The neck portion 204 is located between the upper portion 202 and the bellows portion 208. The neck portion 204 has a diameter that is narrower than both the upper portion 202 and the bellows portion 208. In this embodiment, the diameter of the neck portion 204 is the same as the diameter of the elongate portion 210. The neck portion 204 is adapted to engage with the object 200 to be sterilised. This helps to prevent movement of the object 200 both in the lateral and transverse directions and maintains the object 200 on the platform 302.

To sterilise an object 200, the object 200 is inserted into the internal environment 300 of the container body 102 through the first opening 114. The object engages with the neck portion 204 where it is restrained. The object 200 is then oriented on top of a platform 302 where it engages with the platform 302 to prevent free movement of the object 200. The first opening 114 and the second opening 118 are then sealed by engaging the first cap 106 and the second cap 108 with the first threaded portion 112 and the second threaded portion 116 respectively. After the first cap 106 and the second cap 108 have been applied, the object 200 is sealed within the container 100. The container 100 including the object 200 is then placed within a sterilisation environment so that the object 200 can be sterilised.

As discussed previously, the sterilisation environment may be within an autoclave. In the case of an autoclave, steam at high temperature and pressure is able to enter into the container through the vapour permeable sterility barriers 120 and 122. The high temperature and pressure steam interacts with the object to sterilise it. The steam can then exit through the vapour permeable sterility barriers 120 and 122. It has been found that suitable vapour permeable sterility barriers include the KIMGUARD sterilisation wrap provided by Kimberly-Clark healthcare, or the ASPIRE sterilisation membrane provided by GE. Other means of sterilisation may also be employed. After the sterilisation process has been completed, the container 100 including the sterilised object may be placed into storage for future use.

When use of the object is desired, the first cap 106 is disengaged from the container body 102. Disengagement of the first cap 106 from the container body severs the connection between the first cap 106 and the tamper evident ring 104. This severing in connection indicates that the sterility of the internal environment 300 is no longer being maintained. The bellows portion 208 can then be collapsed such that the first end 201 and the second end 212 are brought relatively closer together such that the object 200 extends out of the first opening 114 and can then be removed from within the internal environment 300 of the container body 102.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A container for sterilising a medical object and storing a sterilised medical object, the container including:
    a container body including a first opening in a first end of the container for passage of the medical object into an internal cavity of the container body, the internal cavity including a removably insertable platform having a receiving surface to receive and support the medical object, the removably insertable platform keyed to be retained in a fixed position between the first end of the container body and a second end of the container body;
    a first seal for closing the first opening; and
    a vapour permeable sterility barrier for maintaining sterility of the internal cavity and allowing passage of vapour;
    wherein the container body is formed from a polymer blend including at least one polymer and a hydrophobic additive.

2. The container of claim 1, wherein the removably insertable platform is additionally keyed to retain the medical object on the surface of the platform.

3. The container of claim 1, wherein the first end of the container and the second end of the container define a longitudinal axis of the container, wherein
    the removably insertable platform has a length that is aligned with the longitudinal axis of the container, and
    the receiving surface of the removably insertable platform is in a plane that faces orthogonal to the longitudinal axis of the container.

4. The container of claim 3, wherein the length of the removably insertable platform extends across at least 50% of the distance between the first end and the second end of the container.

5. The container of claim 1, wherein the vapour permeable sterility barrier is a non-wettable vapour permeable sterility barrier.

6. The container of claim 1, wherein the vapour permeable sterility barrier forms part of the first seal.

7. The container of claim 6, wherein the vapour permeable sterility barrier is insert moulded to the first seal.

8. The container of claim 6, wherein the first seal includes a guard that extends across at least a part of an external surface of the vapour permeable sterility barrier to protect the vapour permeable sterility barrier from damage.

9. The container of claim 2, wherein the removably insertable platform includes drainage holes to prevent a liquid from pooling around the medical object.

10. The container of claim 1, wherein the hydrophobic additive is a fluoro chemical present in the polymer blend at 2 to 5 weight percent.

11. The container of claim 1, further including a second opening in the second end, and a second seal for closing the second opening.

12. The container of claim 11, wherein the vapour permeable sterility barrier forms part of the second seal.

13. The container of claim 1, wherein the vapour permeable sterility barrier is formed from a material selected from the group consisting of polypropylene, polyester and polytetrafluoroethylene.

14. The container of claim 1, wherein the container body further includes a neck portion that is narrower than the container body, the neck portion having an internal surface that engages with the medical object to prevent the medical object from moving within the container.

15. The container of claim 1, wherein the container includes a collapsible or deformable bellows portion.

16. The container of claim 1, the container body including an elongate portion adjacent the second end.

17. The container of claim 1, wherein the removably insertable platform is additionally keyed to retain the medical object on the surface of the platform.

18. The container of claim 17, wherein the first end of the container and the second end of the container define a longitudinal axis of the container, wherein
    the removably insertable platform has a length that is aligned with the longitudinal axis of the container, and
    the receiving surface of the removably insertable platform is in a plane that faces orthogonal to the longitudinal axis of the container.

19. A container for sterilising a medical object and storing a sterilised medical object, the container including:
    a container body including a first opening in a first end of the container for passage of the medical object into an internal cavity of the container body, the internal cavity including a removably insertable platform having a receiving surface to receive and support the medical object, the removably insertable platform keyed to be retained in a fixed position between the first end of the container body and a second end of the container body;
    a first seal for closing the first opening; and
    a vapour permeable sterility barrier for maintaining sterility of the internal cavity and allowing passage of vapour;
    wherein the removably insertable platform is keyed to be retained on the container body via a snap fit mechanism that is directly connected to the container body, which when the snap fit mechanism is engaged the platform is locked in position on the container body.

* * * * *